United States Patent
Seo et al.

(10) Patent No.: US 11,166,684 B2
(45) Date of Patent: Nov. 9, 2021

(54) VARIABLE PET APPARATUS

(71) Applicants: GACHON UNIVERSITY OF INDUSTRY-ACADEMIC COOPERATION FOUNDATION, Seongnam-si (KR); GIL MEDICAL CENTER, Incheon (KR)

(72) Inventors: Seong-Ho Seo, Seoul (KR); Sang-Yoon Lee, Incheon (KR); Jun-Young Chung, Incheon (KR); Ji-Hye Lee, Incheon (KR)

(73) Assignees: Gachon University of Industry-Academic Cooperation Foundation, Seongnam-si (KR); GIL Medical Center, Incheon (KR)

( * ) Notice: Subject to any disclaimer, the term of this patent is extended or adjusted under 35 U.S.C. 154(b) by 0 days.

(21) Appl. No.: 16/304,635

(22) PCT Filed: Oct. 31, 2017

(86) PCT No.: PCT/KR2017/012191
§ 371 (c)(1),
(2) Date: Nov. 26, 2018

(87) PCT Pub. No.: WO2018/080288
PCT Pub. Date: May 3, 2018

(65) Prior Publication Data
US 2019/0274647 A1  Sep. 12, 2019

(30) Foreign Application Priority Data

Oct. 31, 2016 (KR) ........................ 10-2016-0143475

(51) Int. Cl.
*A61B 6/00* (2006.01)
*A61B 6/03* (2006.01)
*G01T 1/29* (2006.01)

(52) U.S. Cl.
CPC .............. *A61B 6/4266* (2013.01); *A61B 6/00* (2013.01); *A61B 6/03* (2013.01); *A61B 6/037* (2013.01); *A61B 6/4411* (2013.01); *G01T 1/2985* (2013.01)

(58) Field of Classification Search
CPC ........... G01T 1/2985; A61B 6/00; A61B 6/03; A61B 6/037; A61B 6/4266; A61B 6/4411
See application file for complete search history.

(56) References Cited

U.S. PATENT DOCUMENTS 5,825,031 A * 10/1998 Wong ...................... G01T 1/164
250/363.03
2002/0148970 A1 * 10/2002 Wong .................... G01T 1/1615
250/394

(Continued)

FOREIGN PATENT DOCUMENTS

KR   10-2009-0097476 A   9/2009
KR      10-1088057 B1   11/2011

(Continued)

*Primary Examiner* — Marcus H Taningco
(74) *Attorney, Agent, or Firm* — Rabin & Berdo, P.C.

(57) ABSTRACT

A variable PET apparatus allows structural changes of detector modules in transversal and longitudinal directions to correspond to various imaging purposes and a cross-sectional diameter of a subject while maintaining an arrangement of the detector modules to be close to a true circle. The variable PET apparatus includes: a gantry having an opening on a longitudinal axis; and detector modules supported on the gantry and arranged a predetermined distance apart from each other such that a detection ring is configured with a diameter in a circumferential direction, wherein the gantry is driven by a gantry drive member, and the detector modules are driven by a detector module drive member. According to the present invention, structural changes of the detector modules in the PET apparatus is possible to correspond to a cross-sectional diameter of a (Continued)

subject without additional devices, thereby improving the spatial resolution and sensitivity.

10 Claims, 11 Drawing Sheets

(56) References Cited

U.S. PATENT DOCUMENTS

| | | | |
|---|---|---|---|
| 2003/0128801 A1* | 7/2003 | Eisenberg | A61B 6/032 378/19 |
| 2012/0165651 A1 | 6/2012 | Yamaya et al. | |
| 2014/0316258 A1* | 10/2014 | Hahn | A61B 6/037 600/427 |
| 2014/0367577 A1* | 12/2014 | Badawi | A61B 6/037 250/366 |
| 2015/0119704 A1* | 4/2015 | Roth | A61B 6/4258 600/425 |
| 2018/0095182 A1* | 4/2018 | Su | G01T 1/2985 |
| 2018/0106913 A1* | 4/2018 | Jiang | G01T 1/2985 |

FOREIGN PATENT DOCUMENTS

| | | |
|---|---|---|
| KR | 10-2011-0130954 A | 12/2011 |
| KR | 10-2011-0130962 A | 12/2011 |

* cited by examiner

VARIABLE PET APPARATUS

TECHNICAL FIELD

The present invention relates to a positron emission tomography (PET) apparatus. More particularly, the present invention relates to a variable PET apparatus geometrically deforming an arrangement of detection modules to correspond to a cross-sectional diameter of a subject.

BACKGROUND ART

Positron emission tomography (PET) is a nuclear medicine functional imaging technique that obtains physiological and biochemical images of the human body in three dimensions using radiopharmaceuticals that emit positrons. These days, PET is widely used in diagnosis of various cancers and is especially known as a useful test for differential diagnosis, staging, evaluation of recurrence, and evaluation of treatment effect, and the like, of cancer. In addition, PET is used to obtain receptor images or metabolic images for diagnosis of cardiac diseases, cerebral diseases, and brain function assessment.

A positron refers to an antiparticle that has physical properties similar to an electron with negative (−) charge, but has positive (+) charge. Positrons are emitted from radioisotopes such as C-11, N-13, O-15, F-18, etc., as one type of radiation. Since such elements are major constitutional elements of biomaterial, a radiopharmaceutical thereof can be utilized as a tracer for tracking a specific physiological, biochemical or functional change. For example, F-18-FDG, a radioactive medicine most frequently used, is a glucose-like material. A large amount of F-18-FDG gathers in a specific area of glucose hypermetabolism such as in cancer when injected in a body.

A positron emitted from radioisotopes consumes all of own kinetic energy in a short time after emission. Then, the positron undergoes annihilation by colliding with neighboring electrons. At this point, two annihilation radiations (511 keV annihilation photons; e.g., gamma-ray) are emitted at an angle of 180°. A PET scanner, which is cylindrical, is a device capable of detecting two annihilation radiations emitted simultaneously. By reconstructing images using radiation detected thereby, it is possible to display by way of a three-dimensional tomographic image used for determining how much and where radiopharmaceuticals are concentrated in the body. A part of the body displaying an abnormally strong signal due to accumulation of radiopharmaceuticals in PET images can subsequently be diagnosed as a cancer.

However, while a PET scanner can provide molecular and functional information for human tissue, there are limits in providing anatomical information due to a low resolution thereof. Therefore, in order to solve the problem, a positron emission tomography-computed tomography (PET-CT) scanner, a positron emission tomography-magnetic resonance imaging (PET-MRI) scanner, etc., which are respectively combined with a computed tomography (CT) scanner or a magnetic resonance imaging (MRI) scanner, are widely used in recent days. In the present description, PET scanners, PET-CT scanners, PET-MRI scanners, etc. are all collectively referred to as "PET apparatus".

Sensitivity and resolution, which are important performance indicators of PET apparatuses, are affected by a geometry of a PET apparatus in accordance with an arrangement of detection modules. Therefore, in order to obtain the best image quality, it is ideal to use equipment that corresponds to the cross-sectional diameter of the subject, from the structural aspect. However, a cross-sectional diameter of a subject may vary depending on purposes of PET imaging. In accordance with this, it is impossible to provide PET apparatuses having different diameters due to cost and space thereof.

There is a related art of variable PET apparatuses. Korean Patent Application Publication No. 10-2011-0130954 published on Dec. 6, 2011 discloses a variable PET apparatus of which a transverse-sectional radius is variable.

However, the efficiency in the longitudinal direction is not considered in the above-mentioned variable PET apparatus. In addition, considering a physical engagement with a driving means driving detection modules, it is impossible to realize the variable PET apparatus because detector heads 102 of a second group come into contact with each other whereby it is impossible to realize a circle with the detector heads 102.

Documents of Related Art

Korean Patent Application Publication No. 10-2011-0130954, published on Dec. 6, 2011

DISCLOSURE

Technical Problem

Accordingly, the present invention has been made keeping in mind the above problems occurring in the related art, and the present invention is intended to provide a variable PET apparatus allowing structural changes of a detection module in transversal and longitudinal directions to correspond to various imaging purposes and a cross-sectional diameter of a subject while maintaining an arrangement of the detection modules to be close to a circle.

Technical Solution

In order to accomplish the above objective, a variable positron emission tomography (PET) apparatus according to the present invention includes: a gantry having an opening on a longitudinal axis; and detection modules supported on the gantry and arranged a predetermined distance apart from each other such that a detection ring is configured having a diameter in a circumferential direction, wherein the gantry is driven by a gantry driving means, and the detection modules are driven by a detection module driving means.

Advantageous Effects

A variable PET apparatus according to the present invention allows structural changes of detection modules in the PET apparatus to correspond to a cross-sectional diameter of a subject without being equipped with additional devices, thereby improving the spatial resolution and sensitivity. In addition, cost can be reduced.

In addition, according to the present invention, a configuration unit of the variable PET apparatus is structurally deformed by miniaturized detection modules such that it is possible to maintain an arrangement of the detection modules to be close to a circle while imaging a subject having a small diameter, such as a brain or a small animal, thereby reducing sensitivity deterioration.

In addition, according to the present invention, a configuration unit of the PET apparatus is structurally deformed by miniaturized detection modules such that it is possible to optimize a cross-sectional diameter of a subject and further improve the sensitivity and resolution.

In addition, according to the present invention, detection modules has a wide width in the longitudinal direction due to radial expansion and contraction motion with respect to the longitudinal axis, as well as due to translational motion of the gantries 110 and 120 along the longitudinal axis. Accordingly, there is an advantage in that a solid angle is increased such that the structural sensitivity can be improved.

In addition, according to the present invention, a gantry is capable of translational motion in the longitudinal direction such that the number of lines of response (LORs), which are required for reconstruction in three dimensions, increases, whereby there is an advantage in that the sensitivity of the PET apparatus can be further improved.

Furthermore, according to the present invention, each detection module can be diversified in longitudinal and transversal directions, thereby minimizing the number of detection modules constituting the PET apparatus and reducing additional cost.

BRIEF DESCRIPTION OF THE DRAWINGS

FIG. 3b is a side view partly illustrating an arrangement of detection modules in the basic structure of a pair of gantries of FIG. 3a;

BEST MODE

Figure 1A:
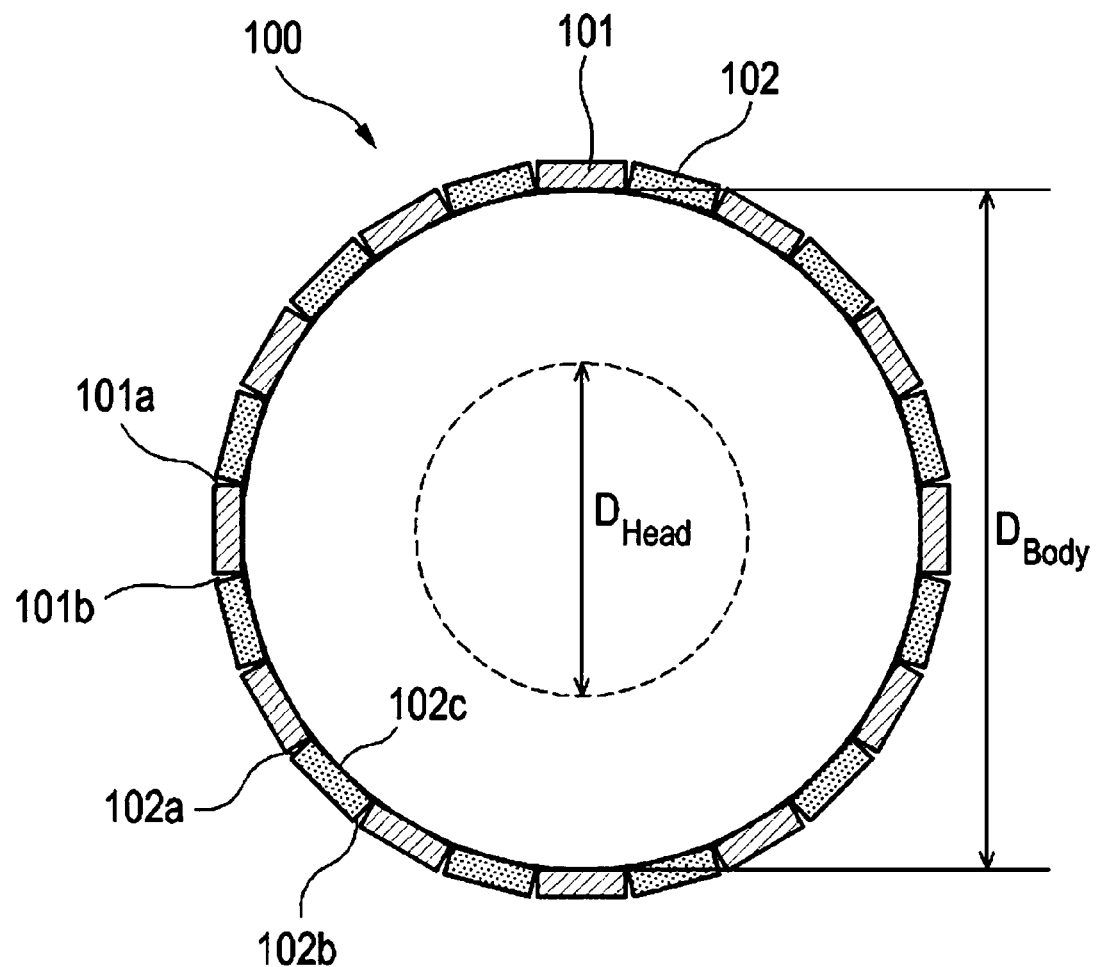
FIGS. 1a and 1b are front views illustrating an operation of a related art of the present invention.
Figure 1B:
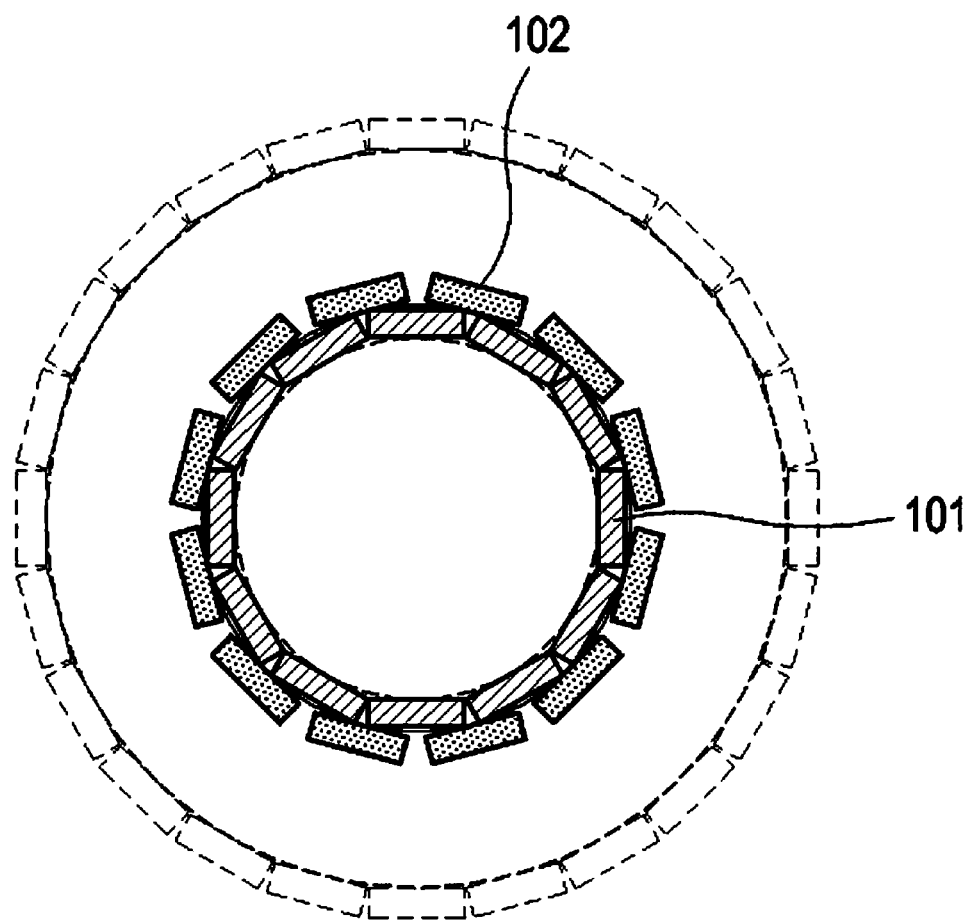

Specific structural and functional descriptions of embodiments of the present invention disclosed herein are only for illustrative purposes of the embodiments of the present invention. The present invention may be embodied in many different forms without departing from the spirit and significant characteristics of the present invention. Therefore, the embodiments of the present invention should not be construed as limiting the present invention, but various modifications, equivalents, additions and substitutions are possible, without departing from the scope and spirit of the invention.

Hereinafter, embodiments of the present invention will be described in detail with reference to the accompanying drawings. Throughout the drawings, the same reference numerals will refer to the same or like parts.

Figure 2:
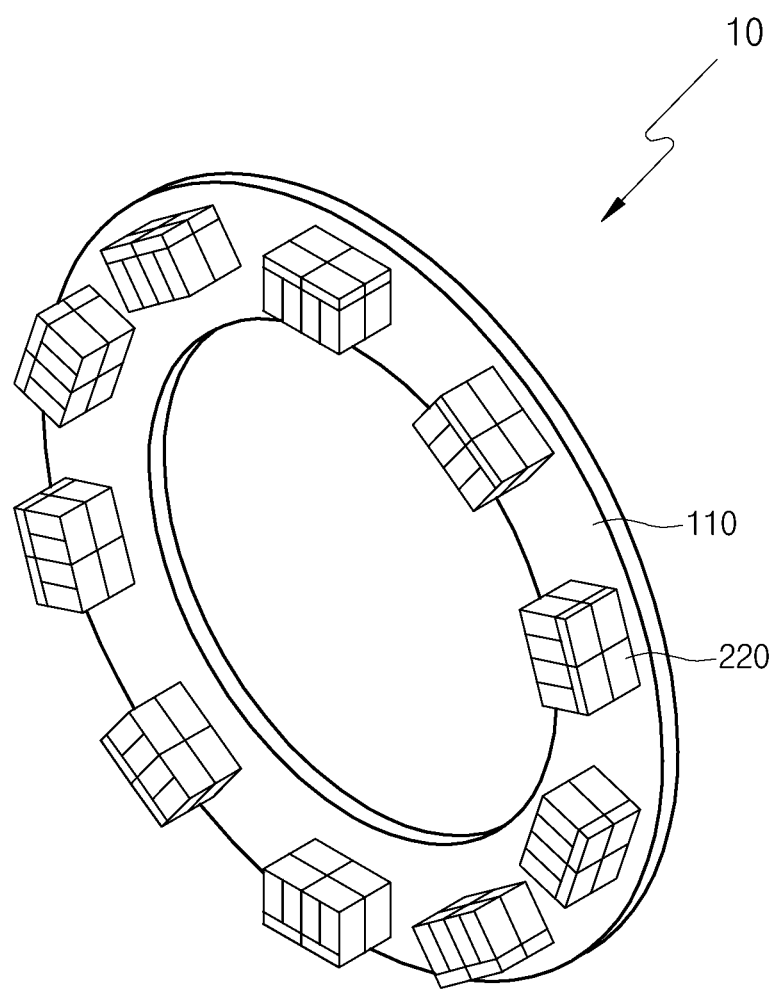
FIG. 2 is a perspective view illustrating a first gantry and a first detection module in a basic structure of a variable positron emission tomography (PET) apparatus according to an embodiment of the present invention.
Figure 3A:
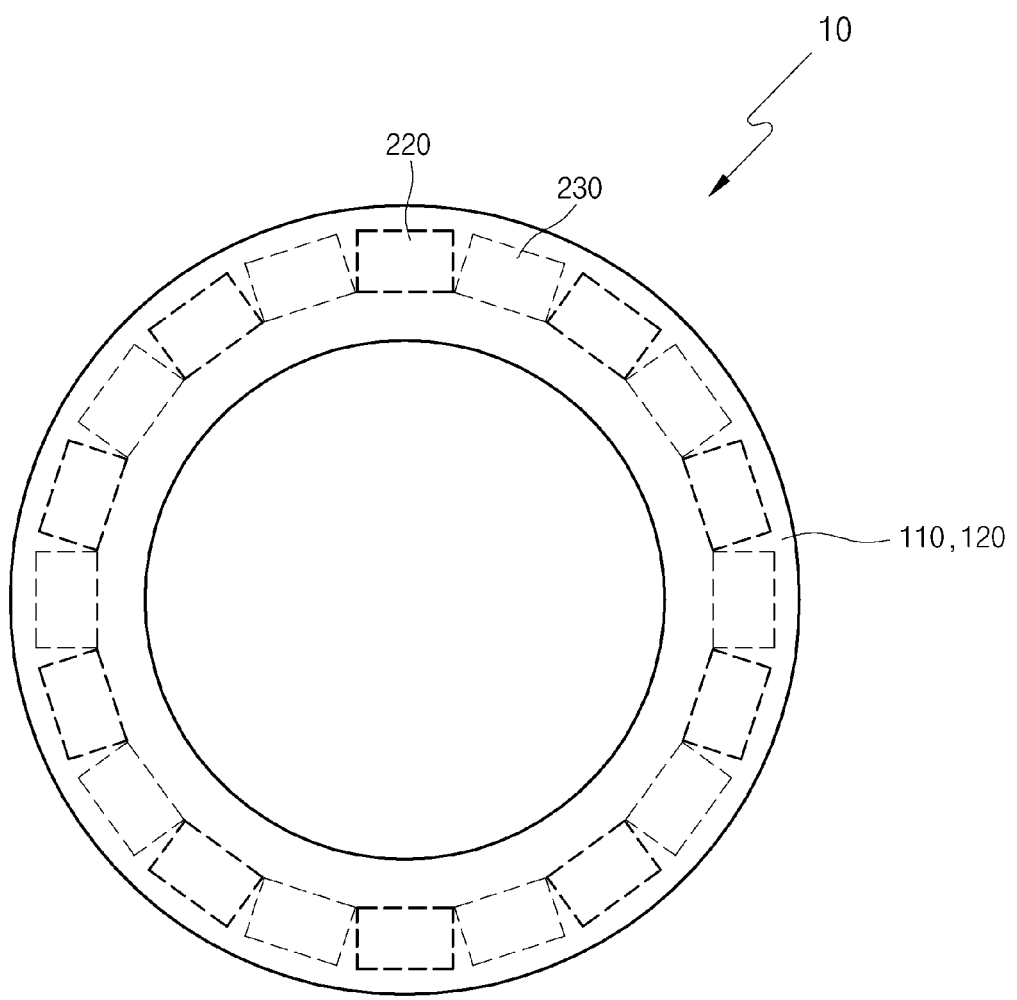
FIG. 3a is a front view illustrating a basic structure of a pair of gantries according to the embodiment of the present invention.
Figure 3B:
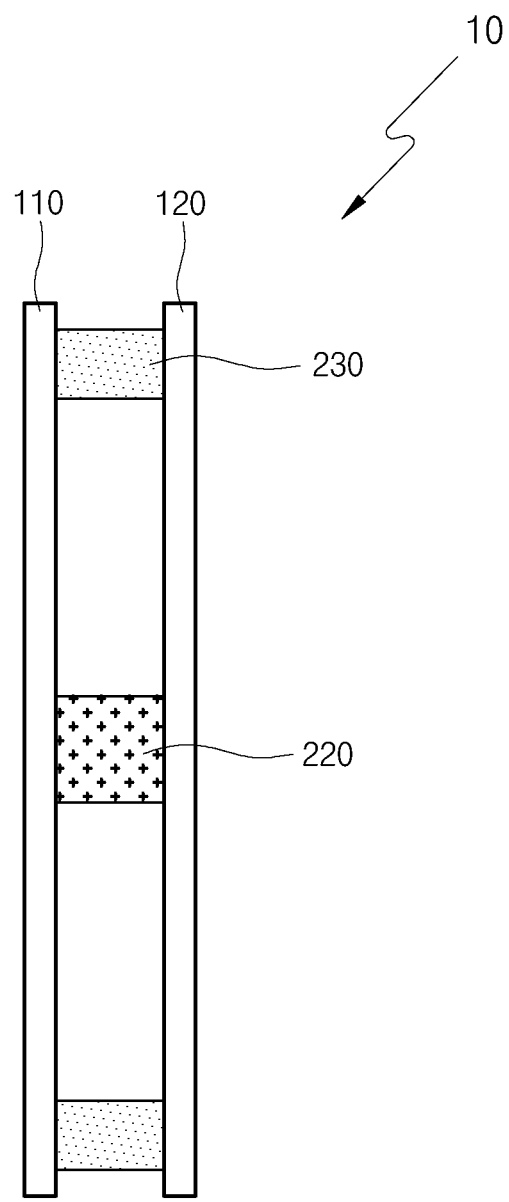
Figure 4A:
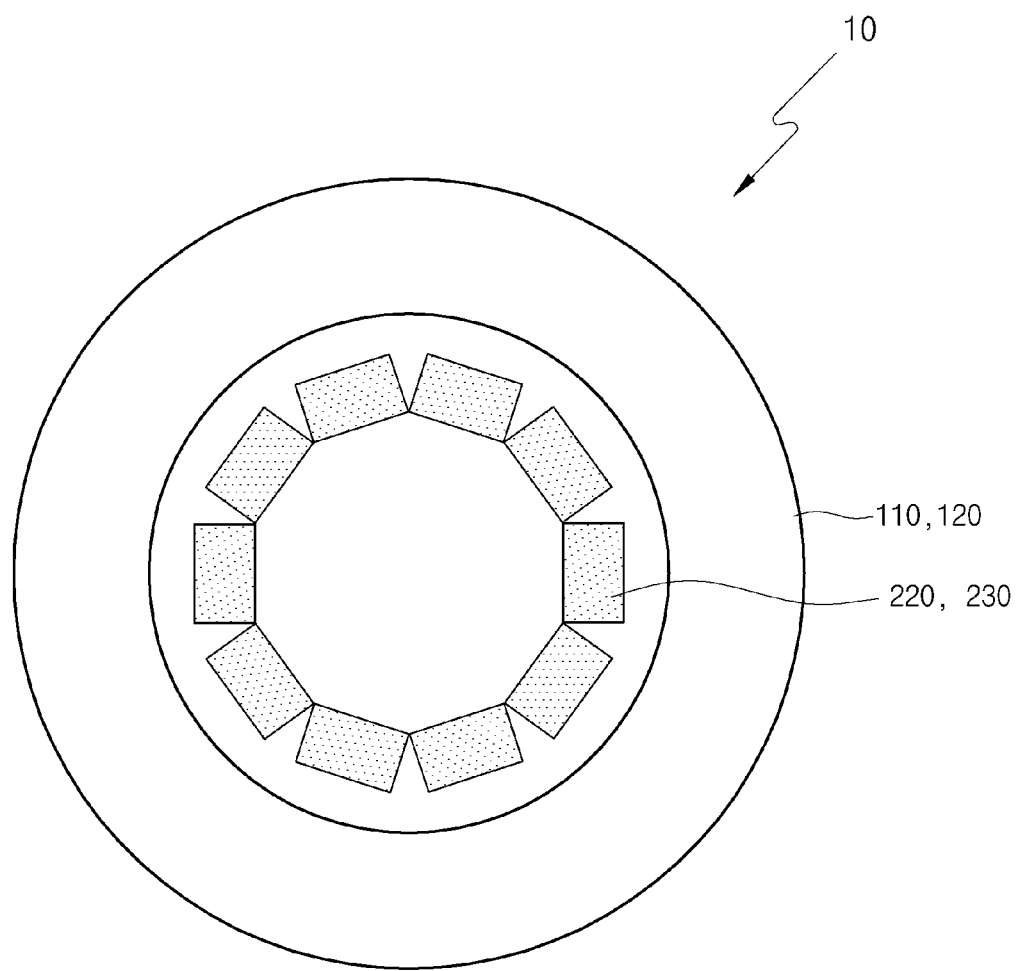
FIG. 4a is a front view illustrating a first moving state of the detection modules according to the embodiment of the present invention.
Figure 4B:
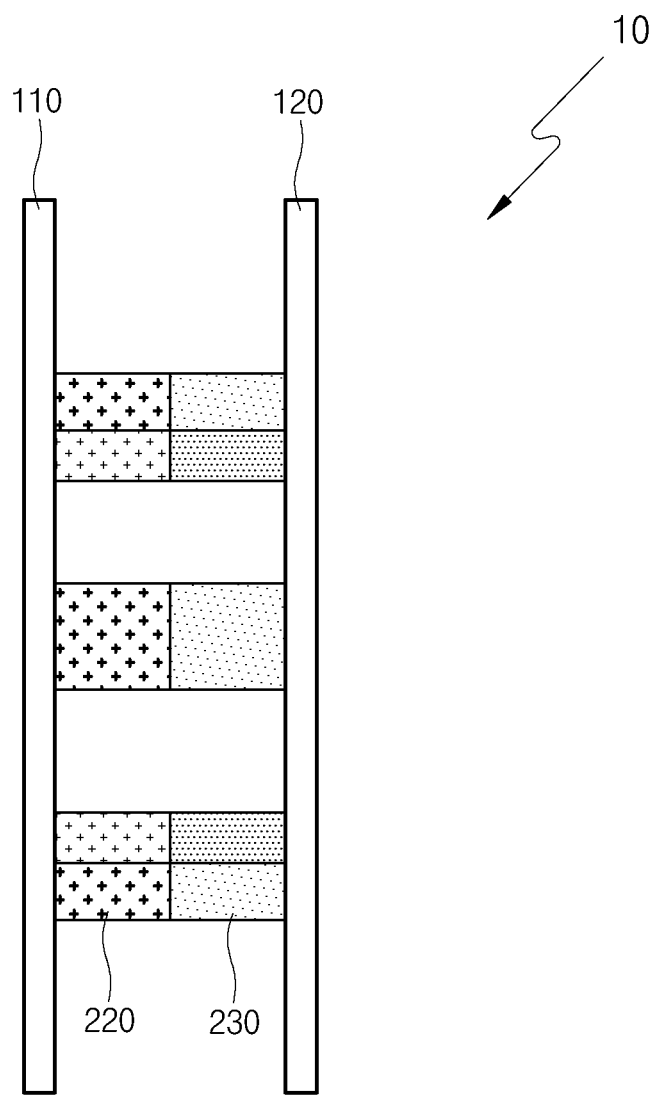
FIG. 4b is a side view partly illustrating an arrangement of the detection modules in the first moving state according to the embodiment of the present invention.
Figure 5A:
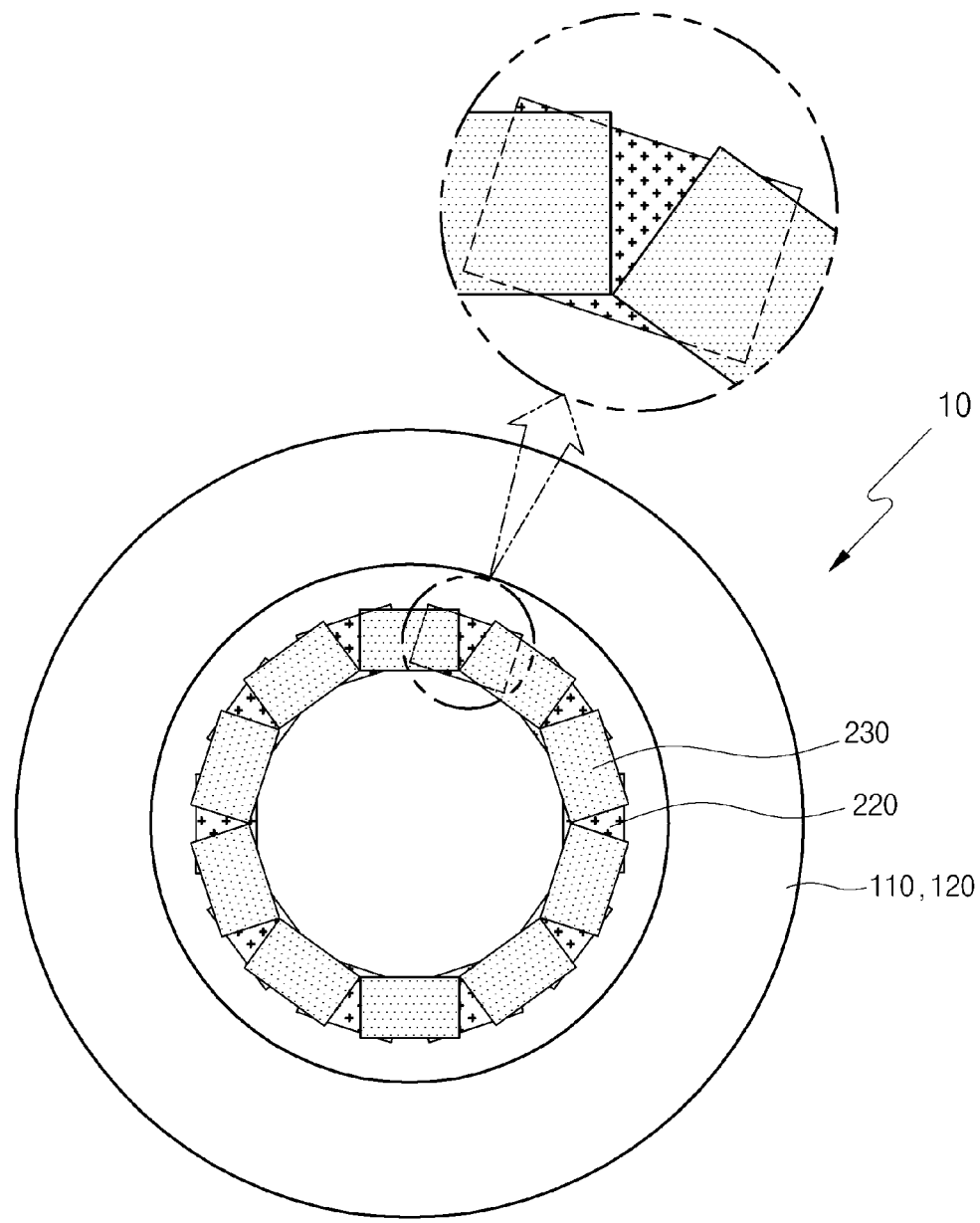
FIG. 5a is a front view illustrating a second moving state of the detection modules according to the embodiment of the present invention.
Figure 5B:
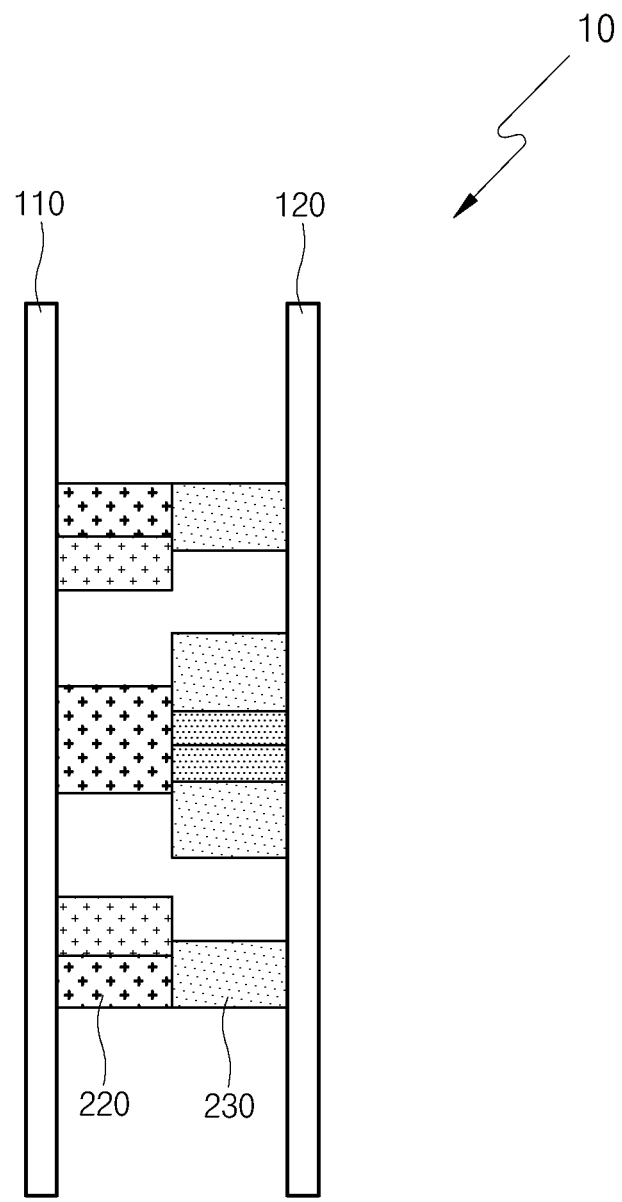
FIG. 5b is a side view partly illustrating an arrangement of the detection modules in the second moving state according to the embodiment of the present invention.
Figure 6A:
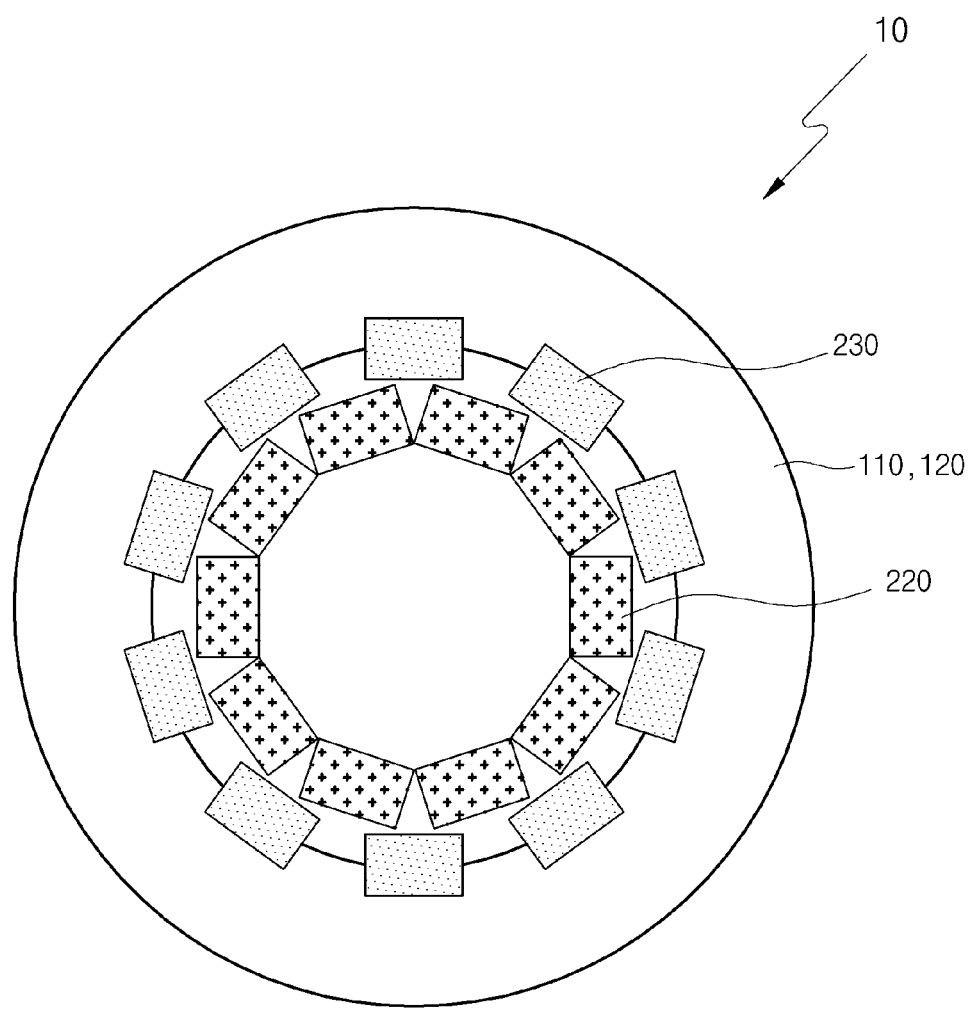
FIG. 6a is a front view illustrating a third moving state of the detection modules according to the embodiment of the present invention.
Figure 6B:
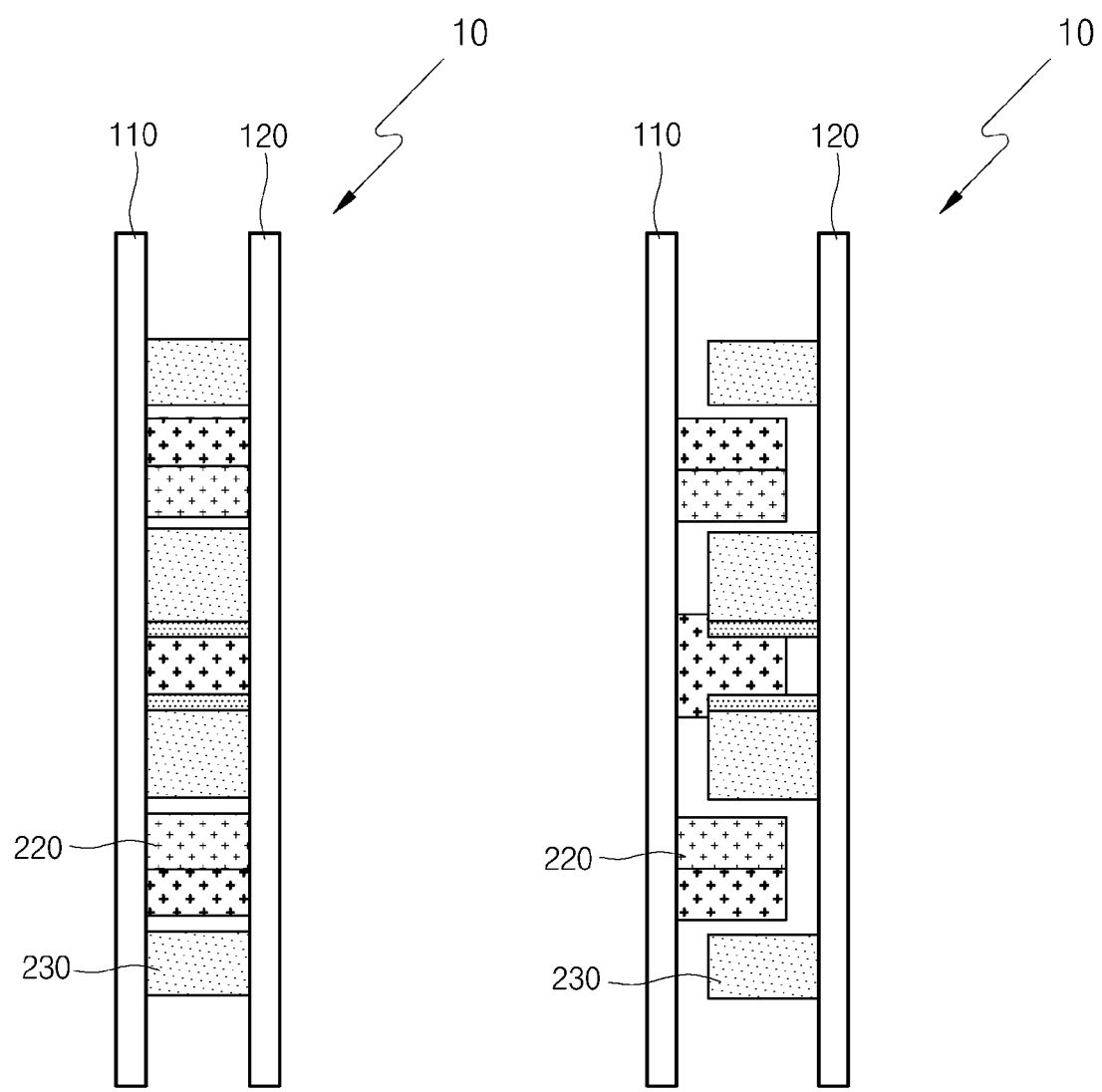
FIG. 6b is a side view partly illustrating an arrangement of the detection modules in the third moving state according to the embodiment of the present invention.

FIG. 2 is a perspective view illustrating a first gantry and a first detection module in a basic structure of a variable positron emission tomography (PET) apparatus according to an embodiment of the present invention; FIG. 3a is a front view illustrating a basic structure of a pair of gantries according to the embodiment of the present invention; FIG. 3b is a side view partly illustrating an arrangement of detection modules in the basic structure of a pair of gantries of FIG. 3a; FIG. 4a is a front view illustrating a first moving state of the detection modules according to the embodiment of the present invention; FIG. 4b is a side view partly illustrating an arrangement of the detection modules in the first moving state according to the embodiment of the present invention; FIG. 5a is a front view illustrating a second moving state of the detection modules according to the embodiment of the present invention; FIG. 5b is a side view partly illustrating an arrangement of the detection modules in the second moving state according to the embodiment of the present invention; FIG. 6a is a front view illustrating a third moving state of the detection modules according to the embodiment of the present invention; and FIG. 6b is a side view partly illustrating an arrangement of the detection modules in the third moving state according to the embodiment of the present invention.

As illustrated in FIGS. 2 to 3b, a variable PET apparatus 10 according to an embodiment of the present invention includes gantries 110 and 120 and detection modules 210. The variable PET apparatus 10 further includes a gantry driving means (not illustrated) and a detection module driving means (not illustrated).

Each of the gantries 110 and 120 has an opening on a longitudinal axis, and the opening has a disc shape. The opening is formed in each of the gantries 110 and 120 to receive a subject to be inspected.

The gantries 110 and 120 are rotatable in a circumferential direction about the longitudinal axis by the gantry driving means (not illustrated). Accordingly, a first gantry 110 and a second gantry 120 rotate to move to positions facing each other as illustrated in FIG. 4a or to be staggered with each other as illustrated in FIG. 3a and FIG. 5a.

In addition, the gantries 110 and 120 are capable of translational motion in the longitudinal direction by the gantry driving means (not illustrated). As illustrated in FIG. 3a, the gantry driving means (not illustrated) moves the detection modules 210 to be positioned with respect to the longitudinal axis in each of the gantries 110 and 120 such that the gantries 110 and 120 have the maximum diameters while moving a first group detection module 220 and a second group detection module 230 facing each other to be in a staggered position and while minimizing a gap between the gantries 110 and 120. Thus, gaps of the first group detection module 220 are filled with gaps of the second group detection module 230 as the detection modules 210 of the facing gantries 110 and 120 mesh with a predetermined area in the same manner a gear wheel does. In this case, a precise design of the gantry driving means (not illustrated) is required to minimize the gap between adjacent detection modules 210.

In the same manner, when the first group detection module 220 and the second group detection module 230 are positioned facing each other, it is preferable to drive the gantry driving means (not illustrated) to minimize a distance between the gantries 110 and 120 such that the first group detection module 220 and the second group detection module 230 come into contact with each other.

As illustrated in FIGS. 3a to 6b, each of the gantries 110 and 120 includes the first gantry 110 and the second gantry 120. The first gantry 110 and the second gantry 120 share the longitudinal axis with each other and are disposed facing each other.

The first gantry 110 include the first group detection module 220 and a first group detection module output signal processing circuit (not illustrated) on a surface thereof and supports the first group detection module 220 and the first group detection module output signal processing circuit. In addition, the gantry driving means (not illustrated) and the detection module driving means (not illustrated) are provided on the surface or an opposite surface.

The second gantry 120 is combined with the second group detection module 230, a second group detection module output signal processing circuit (not illustrated), the gantry driving means (not illustrated), and the detection module driving means (not illustrated). The combined structure thereof is the same as that of the first gantry 110 whereby the description thereof is omitted.

As described above, the detection module 210 according to the present invention has a wide width in the longitudinal direction due to radial expansion and contraction motion with respect to the longitudinal axis, as well as due to translational motion of the gantries 110 and 120 along the longitudinal axis. Accordingly, there is an advantage in that a solid angle is increased such that the structural sensitivity can be improved.

As described above, since the gantries 110 and 120 according to the present invention translate in the longitudinal direction, the number of lines of response (LORs), which are required for reconstruction in three dimensions, increases, whereby there is an advantage in that the sensitivity of the PET apparatus can be further improved.

As illustrated in FIGS. 2 to 6b, the detection modules 210 are disposed on a surface of each of the gantries 110 and 120, supported by the gantries 110 and 120, and disposed in a circumferential shape. Specifically, the detection modules 210 are arranged at regular intervals to form a detection ring in the circumferential direction with a predetermined diameter.

The detection modules 210 detect gamma rays emitted from a subject. The detection modules 210 are arranged to form a detection ring with a predetermined diameter so as surround a subject on the longitudinal axis.

The detection modules 210 are capable of extending and retracting along the longitudinal direction by the detection module driving means (not illustrated). The detection modules 210 implement and maintain a circle-shaped detection ring even in the expansion and contraction motion. The detection modules 210 move constantly by the same distance along the longitudinal direction to maintain the detection ring in a circle structure. Furthermore, the detection modules 210 extend and contract in the radial direction such that the detection ring can have same diameters around the longitudinal axis.

Each of the detection modules 210 includes one or more block detectors 211 on a transverse section. It is preferable that the detection module 210 includes the block detector 211 having a small size such that each of the first gantry 110 and the second gantry 120 is provided with multiple detection modules 210. As each of the gantries 110 and 120 includes the multiple detection modules 210, the entire detection module 210 has a structure close to a circle.

It is preferable that the number of detection modules 210 is large. However, it is preferable to select the number of detection modules 210 appropriately according to a size of the block detectors and a subject.

A subject may take a case in which a whole body is imaged with the detection ring having the largest diameter of about 70 cm to 90 cm, where the detection modules 210 are extended to the maximum value on the basis of the transverse section as illustrated in FIG. 3a. In addition, a brain may be imaged with the detection ring having the smallest diameter of about 40 cm to 50 cm, where the detection modules 210 are contracted to the minimum value as illustrated in FIGS. 4a and 5a. Furthermore, a small animal may be imaged as illustrated in FIG. 6a.

Each of the detection modules 210 includes the multiple block detectors 211. The number of block detectors 211 in the longitudinal direction may correspond to the number of detection rings. It is preferable the number of detection rings is selected considering an imaging range of about 15 cm to 40 cm in the longitudinal axis when imaging a whole body as illustrated in FIG. 3b. It is preferable the number of detection rings is selected considering an imaging range of about 20 cm to 25 cm in the longitudinal axis when imaging a brain or a small animal as illustrated in FIGS. 4b, 5b, and 6b. The cost becomes higher with additional detection modules 210. Therefore, selecting an appropriate number of detection modules 210 is required.

The block detector 211 includes one or more scintillation crystals 212 and a solid state light sensor 213. The scintillation crystal 212 converts gamma rays into light. The solid state light sensor 213 is a device for converting light into an electric signal and may be configured of any one of a photomultiplier tube (PMT), an avalanche photodiode (APD), a silicon photomultiplier (SiPM), or the like.

The detection modules 210 constitute first group detection modules 220 and second group detection modules 230. Here, the first group detection modules 220 constitute one half of the detection modules 210 and the second group detection modules 230 constitute the other half of the detection modules 210, wherein the first group detection modules 220 and the second group detection modules 230 alternate.

The first group detection modules 220 are arranged on the first gantry 110 in a manner that the detection modules 210 are spaced from each other in a circumferential direction. The second group detection modules 230 are arranged on the second gantry 120 in a manner that the detection modules 210 are spaced from each other in a circumferential direction. The detection modules 210 of the first group detection module 220 are arranged into a lattice with respect to the detection modules 210 of the second group detection module 230 and to the circumferential direction.

Adjacent detection modules 210 are arranged at regular intervals and may be arranged such that the intervals therebetween are minimized. Here, the detection modules 210 are arranged on the same circumference to have a shape of a circle.

When the first gantry 110 and the second gantry 120 are arranged facing each other as illustrated in FIG. 3a, the first group detection module 220 and the second group detection module 230 interposed between the first gantry 110 and the second gantry 120 are positioned on the same circumference such that, assuming that the first group detection module 220 is positioned at an odd-numbered position, the second group detection module 230 is sequentially positioned at an even-numbered position. One half of the detection modules 210 constituting the variable PET apparatus 10 are disposed on the first gantry 210 and the other half of the detection modules 210 constituting the variable PET apparatus 10 are disposed on the second gantry 220, alternately.

The first group detection module 220 and the second group detection module 230 may have a ring-shaped or polygonal transverse section perpendicular to the longitudinal axis. As illustrated in FIGS. 3a, 4a, 5a, and 6, the detection modules 210 are arranged at regular intervals by the detection module driving means (not illustrated) such that the detection modules 210 have a structure close to a circle with a constant radius with respect to the longitudinal axis.

The gantry driving means (not illustrated) and the detection module driving means (not illustrated) drive the gantries 110 and 120 and the detection modules 210, respectively. If the first gantry 110 and the second gantry 120 do not interfere with each other during the translational motion while facing each other, the gantry driving means and the detection module driving means are fixedly disposed on any one of end surfaces of the first gantry 110 and the second gantry 120.

The gantry driving means (not illustrated) and the detection module driving means (not illustrated) may be linear motors or ball screws.

That is, as illustrated in FIGS. 3b and 4b, the gantry driving means (not illustrated) allows the gantries 110 and 120 to translate in the longitudinal direction. Further, the gantry driving means (not illustrated) rotates the gantries 110 and 120 in any direction about the longitudinal axis.

The detection module driving means (not illustrated) allows the detection modules 210 to expand and contract in the radial direction around the longitudinal axis. A distance between each detection module 210 and the longitudinal axis varies by the detection module driving member (not illustrated).

As described above, since a configuration unit of the PET apparatus 10 according to the present invention can be structurally modified by the miniaturized detection modules 210, it is possible to optimize the apparatus with respect to a sectional diameter of a subject and further improve the sensitivity and resolution thereof.

Hereinafter, a method of operating a PET apparatus will be described with reference to FIGS. 3a to 6b.

FIGS. 3a and 3b illustrate a configuration of the apparatus suitable for taking an image of a subject having a large diameter, such as a whole body, among variable shapes of the gantries 110 and 120 and the detection module 210 according to the embodiment of the present invention. Each of the detection modules 210 is positioned being spaced a distance of a maximum diameter with respect to the longitudinal axis and the gantries 110 and 120 are arranged to be meshed with each other with a minimum distance from each other.

A first moving state illustrated in FIGS. 4a and 4b represents a configuration of the apparatus suitable for taking an image of a subject having a small diameter, such as a brain or a small animal, among variable shapes of the gantries 110 and 120 and the detection module 210 according to the embodiment of the present invention. The detection modules 210 are arranged to maximally reduce gaps therebetween along the longitudinal axis by the gantry driving means (not illustrated). One or all of the gantries 110 and 120 are rotated by using the gantry driving means (not illustrated) such that the first group detection module 220 and the second group detection module 230 define each circle and face each other, whereby detection modules 210 coming into contact with each other in the longitudinal axis face each other. In addition, the detection modules 210 are positioned to be in contact with each other by using the gantry driving means (not illustrated). As a result, the sensitivity of imaging can be improved by extending the longitudinal length.

A second moving state illustrated in FIGS. 5a and 5b represents a configuration of the apparatus suitable for taking an image of a subject having a small diameter, such as a brain or a small animal, among variable shapes of the gantries 110 and 120 and the detection module 210 according to the embodiment of the present invention. The detection modules 210 are arranged to maximally reduce gaps therebetween along the longitudinal axis by the gantry driving means (not illustrated). One or all of the gantries 110 and 120 are rotated by using the gantry driving means (not illustrated) such that the first group detection module 220 and the second group detection module 230 define each circle and face each other, whereby detection modules 210 coming into contact with each other in the longitudinal axis are staggered with each other. In addition, the detection modules 210 are positioned to be in contact with each other in a staggered manner by using the gantry driving means (not illustrated). As a result, the sensitivity of imaging can be improved by extending the longitudinal length. In addition, when reconstructing a three-dimensional image, the gaps between the detection modules 210 are minimized in the vicinity of the contacts of the first group detection module 220 and the second group detection module 230 whereby an influence occurred due to the presence of the gaps can be minimized.

Furthermore, it is possible to obtain a gap correction effect of the detection modules 210 on the transverse section.

A third moving state illustrated in FIGS. 6a and 6b represents a configuration of the apparatus suitable for taking an image of a subject having a small diameter, such as a brain or a small animal, among variable shapes of the gantries 110 and 120 and the detection module 210 according to the embodiment of the present invention. The detection modules 210 are arranged to partly reduce gaps therebetween along the longitudinal axis by the gantry driving means (not illustrated). Accordingly, the configuration is obtained, which is suitable for imaging a subject that is not long in the longitudinal direction. The first group detection module 220 is moved in the radial direction by the detection module driving means (not illustrated) such that it is possible to position the first group detection module 220 to cover the gaps with the second group detection module 230 having a larger diameter. Here, one or all of the gantries 110 and 120 are rotated by the gantry driving means (not illustrated) to position the first group detection module 220 and the second group detection module 230 in a staggered position. In addition, the gantry driving means (not illustrated) allows translatational motion of one or all of the gantries 110 and 120 such that the second group detection module 230 is positioned to surround the first group detection module 220. Accordingly, it is possible to obtain a gap correction effect due to the double-positioned detection rings 210 and improve the sensitivity thereof.

As described above, the variable PET apparatus 10 according to the present invention allows structural changes of the detection modules 210 in the PET apparatus to correspond to a cross-sectional diameter of a subject without being equipped with additional devices, thereby improving the spatial resolution and sensitivity. In addition, cost can be reduced.

Although the embodiments of the present invention have been disclosed with reference to the accompanying drawings for illustrative purposes, those skilled in the art will appreciate that various modifications, additions and substitutions are possible, without departing from the scope and spirit of the invention as disclosed in the accompanying claims. It is thus well known to those skilled in that art that the present invention is not limited to the embodiment disclosed in the detailed description, and the patent right of the present invention should be defined by the scope and spirit of the invention as disclosed in the accompanying claims.

[Description of reference numerals in the drawings]

| | |
|---|---|
| 10: PET appratus | |
| 110: first gantry | 120: second gantry |
| 210: detection module | 211: block detector |
| 212: scintillation crystal | 213: solid state light sensor |
| 220: first group detection module | 230: second group detection module |

What is claimed is:

1. A variable positron emission tomography (PET) apparatus for scanning a subject, comprising:
a gantry having an opening on a longitudinal axis; and
detection modules supported on the gantry and arranged a predetermined distance apart from each other in a circumferential direction such that a detection ring is configured having a diameter, wherein:
the gantry is driven by a gantry driving means, and the detection modules are driven by a detection module driving means;
the gantry includes a first gantry and a second gantry sharing the longitudinal axis with the first gantry and disposed to face the first gantry;
the detection modules include a first group detection module arranged in the circumferential direction on the first gantry with gaps and a second group detection module spaced apart from the first group detection module arranged in the circumferential direction on the second gantry with gaps;
at least one of the first and second gantries is allowed to translate along the longitudinal axis to adjust a gap between the first and second gantries, and the first and second detection modules are movable in a radial direction with respect to the longitudinal axis or in a direction along the longitudinal axis to be rearranged within the adjusted gap between the first and second gantries,
the diameter of the detection ring and the gap between the first and second gantries are adjustable between
a first position in which the first group detection module and the second group detection module come into contact each other in the direction along the longitudinal axis in two layers including a first layer formed by the first group detection module and a second layer formed by the second group detection module,
a second position in which the detection modules in the first and second group detection modules are arranged to be meshed with each other to form a single detection ring in a single layer that is formed collectively by the first and second group detection modules, and
a third position in which the detection modules in the first group detection module and the detection modules in the second group detection module are arranged in a staggered manner to respectively form detection rings with different diameters in two layers,
wherein the gap between the first and second gantries in the second position is smaller than the gap between the first and second gantries in the first position, and
wherein:
the first group detection module has a first width in the direction along the longitudinal axis, and the second group detection module has a second width in the direction along the longitudinal axis, a width of a combination of the first and second group detection modules in the direction along the longitudinal axis is adjustable such that:
in the first position, the width of the combination of the first and second group detection modules arranged in the two layers is sum of the first width and the second width; and
in the second position, the width of the combination of the first and second group detection modules meshed to form the single layer is either the first width or the second width.

2. The apparatus of claim 1, wherein the first group detection module and the second group detection module have a ring-like or polygonal transverse section.

3. The apparatus of claim 1, wherein the gantry is rotatable in the circumferential direction about the longitudinal axis by the gantry driving means.

4. The apparatus of claim 1, wherein each of the detection modules includes multiple block detectors,
wherein the block detector includes:
one or more scintillation crystals; and
a solid state light sensor.

5. The apparatus of claim 1, wherein the detection modules are allowed to extend and retract about the longitudinal direction by the detection module driving means.

6. The apparatus of claim 5, wherein the detection modules translate by the same distance in the longitudinal direction such that the detection ring is maintained in a circle shape.

7. The apparatus of claim 5, wherein the detection modules move by the same radius around the longitudinal axis such that the detection ring is maintained in a circle shape.

8. The apparatus of claim 1, wherein
the detection modules included in the second group detection module are arranged in the circumferential direction apart from each other with the gaps on the second gantry, and
the first group detection module is movable in the radial direction such that the first group detection module fills said gaps between the detection modules of the second group detection module in the second position.

9. The apparatus of claim 1, wherein the first and second group detection modules are movable such that the second group detection module is positioned to surround a ring-like shape formed by the first group detection module in the third position.

10. The apparatus of claim 1, wherein the first width is same as the second width.

* * * * *